United States Patent [19]

Yokoyama et al.

[11] Patent Number: 4,619,823
[45] Date of Patent: Oct. 28, 1986

[54] RADIOACTIVE IODINE LABELED METARAMINOL AND DIAGNOSTIC AGENT CONTAINING PLATELETS LABELED THEREWITH

[75] Inventors: Akira Yokoyama, Ohtsu; Yoshiro Ohmomo, Kyoto, both of Japan

[73] Assignee: Nihon Medi-Physics Co., Ltd., Hyogo, Japan

[21] Appl. No.: 564,653

[22] Filed: Dec. 22, 1983

[30] Foreign Application Priority Data

Sep. 9, 1983 [JP] Japan ................................ 58-167339

[51] Int. Cl.[4] ...................... A61K 43/00; A61K 49/00; C07C 131/00
[52] U.S. Cl. ......................................... 424/1.1; 424/9; 564/258; 564/264
[58] Field of Search .................... 424/1.1, 9; 564/258, 564/264

[56] References Cited

U.S. PATENT DOCUMENTS

| | | | |
|---|---|---|---|
| 1,995,709 | 3/1935 | Hartung | 564/364 |
| 3,542,870 | 11/1970 | Fourneau et al. | 564/364 |
| 3,574,211 | 4/1971 | Keck | 564/364 |
| 3,991,173 | 11/1976 | Sinn et al. | 424/1.1 |
| 4,298,591 | 11/1981 | O'Brien, Jr. et al. | 424/1.1 |
| 4,430,319 | 2/1984 | Blau et al. | 424/1.1 |

OTHER PUBLICATIONS

Dewanjee et al, from Radiopharmaceuticals II: Proceedings 2nd Int. Symposium on Radiopharmaceuticals, Mar. 19–22, 1979, Seattle, Washington, Society of Nuclear Medicine, New York, pp. 361–374.

*Primary Examiner*—Christine M. Nucker

[57] ABSTRACT

A radioactive diagnostic agent which comprises platelets labeled with radioactive iodine atom-labeled metaraminol in an aqueous medium.

5 Claims, No Drawings

RADIOACTIVE IODINE LABELED METARAMINOL AND DIAGNOSTIC AGENT CONTAINING PLATELETS LABELED THEREWITH

The present invention relates to a radioactivity-labeled platelet preparation. More particularly, it relates to a radioactivity-labeled platelet preparation, which is useful for nuclear medical diagnosis, and a radioactive iodine atom-labeled compound for said preparation.

Radioactivity labeled fibrinogen is frequently used as the radioactive diagnostic agent for detection of thrombosis. For the diagnosis of artery thrombosis, a radioactivity-labeled platelet preparation has recently been developed wherein the labeling is effected by the use of indium-111 ($^{111}$In) labeled oxine. While the diagnosis of artery thrombosis can be successfully accomplished with this preparation, the following defects are recognized in respect to using such preparation: (1) since labeling is required to be effected in the absence of blood plasma, the physiological activity of radioactivity-labeled platelets is markedly lost; (2) oxine has a relatively high toxicity which can not be disregarded; (3) in the manufacture of the preparation, it is essential to use an organic solvent, which is completely removed from the ultimate preparation only with difficulty; (4) the half life period of indium-111 is relatively long (i.e. 2.81 days), etc.

As a result of a extensive study, there has now been provided a novel radioactivity-labeled platelet preparation which does not have the defects associated with conventional radioactivity-labeled platelet preparation using indium-111 labeled oxine.

The radioactivity-labeled platelet preparation of the present invention comprises platelets labeled with radioactive iodine atom-labeled metaraminol (i.e. alpha-(1-aminoethyl)-3-hydroxybenzenemethanol). It is advantageous that labeling of metaraminol with at least one radioactive iodine atom as well as labeling of platelets with radioactive iodine atom-labeled metaraminol can be accomplished by a simple operation within a short period of time. It is also advantageous that the physiological activity of platelets can be maintained without any material reduction even after said labeling. It is still another advantage that when administered to a living mammal, the platelet preparation shows a high accumulation rate on thrombosis with rapid blood clearance and without specific accumulation on any other organ or tissue. It is a further advantage that metaraminol itself is commercially available as a blood pressure elevating agent, and no practical toxicity problem arises from its use.

Labeling of metaraminol with a radioactive iodine atom can be achieved by a procedure as conventionally adopted for labeling of an organic compound with an iodine atom so as to replace a hydrogen atom on the benzene ring with the radioactive iodine atom. One of typical procedures is the so-called "chloramine T method" wherein metaraminol is iodinated with radioactive iodine atom in a water-soluble salt form (e.g. sodium iodide) in the presence of chloramine T as an oxidizing agent in an aqueous medium. Another typical procedure is an enzymatic method wherein lactoperoxidase is used as an oxidizing agent. Another suitable procedure is an iodine chloride method wherein iodine chloride containing radioacitve iodine is used as an iodinating agent. The resulting aqueous solution containing radioactive iodine atom-labeled metaraminol may be, when desired, passed through a membrane filter to eliminate contaminating organisms.

Manufacture of the radioactivity-labeled platelet preparation may be carried out, for instance, by the following procedure: adding the above prepared aqueous solution containing radioactive iodine atom-labeled metaraminol to blood from which red and white corpuscles were previously eliminated by centrifugation in the presence of an anti-coagulating agent; incubating the resultant mixture, followed by centrifugation to collect platelets labeled with radioactive iodine atom-labeled metaraminol aseptically; and dispersing the collected labeled platelets into an aqueous medium. The above labeling is attained by the affinity of radioactive iodine atom-labeled metaraminol to the serotonin-receptor in platelets.

As explained above, the radioactive iodine atom-labeled metaraminol is usually provided in the form of an aqueous solution and may be used as such for labeling of platelets. However, it may be provided in any other form convenient for the practice of this invention. For instance, said aqueous solution may be subjected to lyophilization, evaporation under reduced pressure at low temperature or the like to obtain a dried product, which also can be used as such or in the form of a solution for labeling. When desired, said aqueous solution or said dried product may be incorporated with any additive such as a pH controlling agent (e.g. an acid, a base, a buffer), a stabilizer (e.g. ascorbic acid), an isotonizing agent (e.g. sodium chloride) or a preserving agent (e.g. benzyl alcohol).

The radioactivity-labeled platelet preparation is also normally provided in the form of an aqueous solution and may be used as such a radioactive diagnostic agent. However, it may be provided in any other form convenient for the practice of this invention. When desired, said aqueous solution may be incorporated with any additive such as a pH controlling agent, a stabilizer, an isotonizing agent or a preserving agent.

The radioactive iodine atom may be any iodine atom having radioactivity. Preferred are iodine-125 ($^{125}$I), iodine-131 ($^{131}$I), iodine-123 ($^{123}$I), etc. Particularly preferred is iodine-123 ($^{123}$I) for reducing the exposure to radioactivity, enhancing the quality of the diagnostic image, etc.

The radioactivity-labeled platelet preparation of the invention should have sufficient radioactivity and radioactivity concentration to assure reliable diagnosis. Simultaneously, however, the radioactivity to which a patient is exposed should be kept as low as possible. In case of the radioactive iodine atom being $^{123}$I, for instance, it may be included usually in an amount of 0.05 to 10 mCi in about 0.5 to 5.0 ml at the time of administration.

As stated above, the radioactivity-labeled platelet preparation of the invention is useful as a radioactive diagnostic agent for thrombosis. It may be also used for detection of cancers, tumors, inflammations, etc.

Practical and presently preferred embodiments of the invention are illustratively shown in the following Examples.

EXAMPLE 1

Manufacture of a radioactive iodine atom-labeled metaraminol preparation:

To 0.2 ml of a solution of metaranaminol ($5 \times 10^{-6}$ mol/ml) dissolved in borate buffer ($1 \times 10^{-6}$ mol), a solution of $^{125}$I-labeled sodium iodide in 0.1 N sodium hydroxide solution (10 mCi; 100 μl) was added, followed by agitation. To the resulting mixture, 0.3 ml of chloramine T ($2\times10^{-6}$ mol) was added, followed by stirring at room temperature for 20 minutes. After completion of the reaction, 0.2 ml of sodium metabissulfite ($2\times10^{-6}$ mol) was added thereto to stop the reaction. The reaction mixture was passed through a column packed with an anion exchange resin (10×3 cm) and eluted with 0.01 N hydrochloric acid to obtain an aqueous solution containing $^{125}$I-labeled metaraminol.

Labeling yield: 93%
Purity: more than 99%
Thin layer chromatography: retention layer, silica gel; solvent, methanol:acetic acid=100:1; Rf=0.5 (liberating iodine ion, Rf=0.75).

The $^{125}$I-labeled metaraminol solution was diluted with 0.01 N hydrochloric acid to make a radioactivity concentration of 1 mCi/ml, and the resulting solution was subjected to filtration through a membrane filter of 0.22 micron in pore size to eliminate contaminating organisms, whereby a $^{125}$I-labeled metaraminol preparation was obtained.

EXAMPLE 2

Change of the take up rate of $^{125}$I-labled metaraminol into platelets in coexistence with of a medical compound:

The take up rate of $^{125}$I-labeled metaraminol into platelets in the coexistence with a medical compound was examined. Calculation was make taking the take up rate in case of $^{125}$I-labeled metaraminol alone as 100%. $^{125}$I-labeled metaraminol was added to platelets in a molar concentration of $1\times10^{-7}$. The results are shown in Table 1 wherein the value indicates the average of three cases.

TABLE 1

| Medical compound | Amount added (molar concentration) | Take up rate (%) |
|---|---|---|
| Quabain | $1\times10^{-5}$ | 58.7 ± 10.2 |
| Reserpine | $1\times10^{-7}$ | 47.3 ± 6.1 |
| Imipramine | $1\times10^{-4}$ | 45.8 ± 6.3 |
| Serotonin | $1\times10^{-4}$ | 17.1 ± 10.3 |
| Adrenaline | $1\times10^{-4}$ | 61.6 ± 8.3 |
| Propranolol | $1\times10^{-4}$ | 18.0 ± 3.1 |
| Phentolamine | $1\times10^{-4}$ | 43.1 ± 3.4 |

From the above results, it is understood that $^{125}$I-labeled metaraminol has a high directivity (or affinity) to serotonin-receptor.

EXAMPLE 3

Manufacture of a radioactivity-labeled platelet preparation:

Rabbit blood (10 ml) incorporated with an anticoagulating agent was centrifuged at 1200 rpm for 10 minutes, and a plasma abundant in platelets (hereinafter referred to as "PRP") was collected. The PRP (1 ml) was incubated at 37° C. for 10 minutes, the $^{125}$I-labeled metaraminol solution (1 mCi) as obtained in Example 1 was added thereto, and the resultant mixture was incubated at 37° C. for 30 minutes, followed by centrifugation at 3400 rpm for 7 minutes to obtain platelets labeled with $^{125}$I-labeled metaraminol. Labeling yield, 44%.

The above obtained labeled platelets were dissolved in a physiological saline solution containing an anticoagulating agent to obtain a concentration of 0.4 mCi/ml, whereby a radioactivity-labeled platelet preparation was obtained.

All the above operations were carried out aseptically.

EXAMPLE 4

Agglutination of a radioactivity-labeled platelet preparation:

Certain identical amounts of the radioactivity-labeled platelet preparation as obtained in Example 3 and of platelets (having the same solvent system as above except non-labeling) were taken, and their light transmissions (corresponding to agglutination rates) in the presence of different concentrations of adenosine diphosphate were measured. The changes (%) of the light transmissions are shown in Table 2 wherein each value indicates the average of 5 to 8 measurements.

TABLE 2

| Sample | Added amount of adenosine diphosphate (molar concentration) | | |
|---|---|---|---|
| | $5\times10^{-6}$ | $20\times10^{-6}$ | $50\times10^{-6}$ |
| Radioactivity-labeled platelet preparation | 74.6 ± 2.5 | 81.1 ± 4.3 | 84.3 ± 5.5 |
| Platelets | 73.0 ± 4.9 | 80.2 ± 7.0 | 84.4 ± 7.0 |

From the above results, it is understood that platelets labeled with $^{125}$I-labeled metaraminol have substantially the same physiological activity as platelets do.

EXAMPLE 5

Behavior of a radioactivity-labeled platelet preparation in thrombosized rabbits:

Thrombosis was produced at the femoral vein in rabbits by application of formalin thereto. To each of the rabbits, 0.5 ml (0.2 mCi) of the radioactivity-labeled platelet preparation obtained in Example 3 was administered through the ear vein. Thirty minutes or 1 hour after the administration, a certain amount of the blood was sampled, and the thrombotic site was taken out immediately. Radioactivity was measured on the blood and the thrombotic site, and the radioactivity in the same weight of them is shown in Table 3 wherein each value indicates the average on 3 to 4 animals.

TABLE 3

| Sample | Time lapsed after administration | |
|---|---|---|
| | 30 minutes | 60 minutes |
| Radioactivity-labeled platelet preparation | 19.2 ± 4.3 | 62.6 ± 45. |

From the above results, it is understood that the radioactivity-labeled platelet preparation is quite useful as a radioactive diagnostic agent for detection of thrombosis.

EXAMPLE 6

Manufacture of a radioactive iodine atom-labeled metaraminol preparation and a radioactivity-labeled platelet preparation:

In the same manner as in Example 1 but using $^{123}$I in place of $^{125}$I, there was manufactured a radioactive iodine atom-labeled metaraminol preparation.

In the same manner as in Example 3 but using the radioactive iodine atom-labeled metaraminol preparation as obtained above in place of the radioactive iodine atom-labeled metaraminol preparation as obtained in Example 3, there was manufactured a radioactivity-labeled platelet preparation.

EXAMPLE 7

Properties of $^{123}$I-labeled metaraminol and a radioactivity-labeled platelet preparation:

The $^{123}$I-labeled metaraminol and the radioactivity-labeled platelet preparation as obtained in Example 6 were examined respectively in the same manner as in Examples 2 and 4 and confirmed to afford substantially the same results as in those Examples.

Namely, the change of the take up rate of $^{123}$I-labeled metaraminol into platelets in the coexistence with a medical compound is substantially the same as that of $^{125}$I-labeled metaraminol, and the agglutination of platelets labeled with $^{123}$I-labeled metaraminol is substantially the same as that of platelets labeled with $^{125}$I-labeled metaraminol.

EXAMPLE 8

Behavior of a radioactivity-labeled platelet preparation in thrombosized rabbits:

In the same manner as in Example 5, the behavior of the radioactivity-labeled platelet preparation as obtained in Example 6 in thrombosized rabbits was examined, and the nearly same results as in Example 5 were obtained.

Namely, the radioactivity-labeled platalet preparation as obtained in Example 6 is useful as a radioactive diagnostic agent for detection of thrombosis.

EXAMPLE 9

Stability of a radioactive iodine atom-labeled metaraminol preparation:

The radioactive iodine atom-labeled metaraminol preparation as obtained in Example 1 was stored at room temperature (24° to 27° C.) for one month. The resulting preparation was developed on thin layer chromatography as shown in Example 1, and its directivity to serotonin-receptor was examined as shown in Example 2. In both cases, the obtained results were substantially the same as obtained with the radioactive iodine atom-labeled metaraminol preparation immediately after the manufacture. Thus, no change in stability was observed even after the storage over a period of one month.

EXAMPLE 10

Toxicity of a radioactivity-labeled platelet preparation:

In the animal test as in Example 5, no side effect such as convulsions, shock symptoms and color change in organs and tissues was observed.

Even when platelets labeled with $^{125}$I-labeled metaraminol were administered intravenously to three rabbits (bodyweight, about 2 kilograms) in an amount of three times the dose in Example 5, no abnormality was produced over a period of at least one month. Thus, the radioactivity-labeled platelet preparation as obtained in Example 3 has no material toxicity.

What is claimed is:

1. Metaraminol labeled with radioactive iodine by replacement of at least one hydrogen in the metaraminol benzene ring.
2. A platelet labeled with the labeled metaraminol as claimed in claim 1.
3. A radioactive diagnostic agent which comprises the labeled platelet as claimed in claim 2 in a physislogically acceptable aqueous medium.
4. A method for labeling of platelets which comprises contacting platelets with the labeled metaraminol as claimed in claim 1.
5. A method for detection of a diseased site in a patient which comprises administering the radioactive diagnostic agent as claimed in claim 3 to the patient and detecting the diseased site.

* * * * *